US010413487B2

(12) United States Patent
Chen et al.

(10) Patent No.: US 10,413,487 B2
(45) Date of Patent: Sep. 17, 2019

(54) NAIL GEL POLISH AND ITS MANUFACTURING METHOD

(71) Applicant: Shanghai O'Nine Technologies Ltd., Shanghai, Shanghai (CN)

(72) Inventors: Laipeng Chen, Shanghai (CN); Mingtai Ge, Shanghai (CN); Yueyun Dong, Shanghai (CN)

(73) Assignee: SHANGHAI O'NINE TECHNOLOGIES LTD., Shanghai (CN)

( * ) Notice: Subject to any disclaimer, the term of this patent is extended or adjusted under 35 U.S.C. 154(b) by 0 days.

(21) Appl. No.: 16/268,356

(22) Filed: Feb. 5, 2019

(65) Prior Publication Data

US 2019/0167538 A1 Jun. 6, 2019

Related U.S. Application Data

(63) Continuation-in-part of application No. 15/215,555, filed on Jul. 20, 2016, now abandoned.

(30) Foreign Application Priority Data

Dec. 1, 2015 (CN) .......................... 2015 1 0867377

(51) Int. Cl.
| | | |
|---|---|---|
| *A61K 8/04* | (2006.01) |
| *A61K 8/55* | (2006.01) |
| *A61K 8/35* | (2006.01) |
| *A61K 8/49* | (2006.01) |
| *A61Q 3/02* | (2006.01) |
| *A61K 8/81* | (2006.01) |
| *A61K 8/87* | (2006.01) |
| *A61K 8/893* | (2006.01) |

(52) U.S. Cl.
CPC ................ *A61K 8/042* (2013.01); *A61K 8/35* (2013.01); *A61K 8/4913* (2013.01); *A61K 8/55* (2013.01); *A61K 8/817* (2013.01); *A61K 8/8152* (2013.01); *A61K 8/87* (2013.01); *A61Q 3/02* (2013.01); *A61K 8/893* (2013.01); *A61K 2800/412* (2013.01); *A61K 2800/43* (2013.01); *A61K 2800/48* (2013.01); *A61K 2800/54* (2013.01); *A61K 2800/805* (2013.01); *A61K 2800/95* (2013.01)

(58) Field of Classification Search
None
See application file for complete search history.

(56) References Cited

U.S. PATENT DOCUMENTS

| | | |
|---|---|---|
| 5,120,529 A | 6/1992 | Koch |
| 7,645,444 B2 | 1/2010 | Malnou |
| 2011/0182837 A1 | 7/2011 | Steffier |

FOREIGN PATENT DOCUMENTS

| | | |
|---|---|---|
| CA | 1269940 | 6/1990 |
| WO | WO 2007064687 | 6/2007 |

*Primary Examiner* — Robert A Wax
*Assistant Examiner* — Danah Al-Awadi
(74) *Attorney, Agent, or Firm* — Dragon Sun Law Firm, PC; Jinggao Li, Esq.

(57) ABSTRACT

A UV/LED radiation-curable nail gel polish composition, method and the use thereof. The composition is comprised of oligomers and monomers and specially obtaining alcohol soluble thermoplastic resins. The advantage of this method is making the removing of the polymerized nail gel polish by medical alcohol easier and safer.

8 Claims, 2 Drawing Sheets mixing and dissolving 2,4,6-trimethylbenzoyldiphenyl-phosphine oxide and 1-hydroxy-cyclohexylphenyl-ketone (photo-initiator), mono-functional (methyl)acrylate monomer and bis-functional (methyl)acrylate monomer under 1000-2000 rpm for 20 minutes in the reaction kettle until it forms uniform viscous liquid

keeping stirring condition, adding in turn aliphatic (methyl)acrylate polyurethane, alcohol soluble thermoplastic resin 1 or resin 2 or resin 3, copolymers containing pigment affinity group, then mixing and dissolving under 1000rpm~2000rpm for 20~25min in reaction kettle; adding in turn polyether silicone wetting agent and polyether modified silicone fluid levelling agent; and mixing and dissolving under 1000rpm~2000rpm for 20~25min in reaction kettle

adding in turn red pigment, polymer-type defoamer without organic Silicon, mixing and dissolving; then putting them in sand mill to grind for 30 minutes until pigment particle size is less than 20 microns and obtaining the nail gel polish

FIG. 2

NAIL GEL POLISH AND ITS MANUFACTURING METHOD

CROSS-REFERENCE TO RELATED APPLICATIONS

The present application is continuation-in-part application of U.S. patent application Ser. No. 15/215,555, filed on Jul. 20, 2016, which claimed the benefit of Chinese Patent Application No. 201510867377.1, filed on Dec. 1, 2015. The present application claims priority to and the benefit of U.S. patent application Ser. No. 15/215,555 and Chinese Patent Application No. 201510867377.1. The entire disclosures of the above-identified applications are incorporated herein by reference.

FIELD OF THE DISCLOSURE

This disclosure relates to the field of UV/LED radiation-curable gels used for cosmetic nail decorative products, and particularly relates to a nail gel polish and its manufacturing method.

BACKGROUND OF THE DISCLOSURE

The nail coatings used in human finger mainly are gel polish and nail lacquer. Compared with nail lacquer, the advantages of nail gel polish include, but not limited to, the shorter time of forming film, the longer time holding on fingers, etc.

The gel polish gives very good adhesion on natural nails, artificial fingernails, toenails and artificial nail extensions. However, when we want to remove the polymerized nail coating, it brings too much difficulties. In general, there are two popular removing methods: one is mechanic sanding, and the other is using removing solvent. For the former removing method, a skilled craft and a professional device are needed. If one person is not skilled at sanding nail gel, nails may become thinner and more brittle than before. What is worse is that the customers may feel painful after services. If removing solvent mixture is utilized, the main components of removing liquid are solvent like acetone, ethyl acetate or butyl acetate, and they are with pungent odor. And additionally, the volatile organic solvent may cause harmful disease to human organs such as skin and respiratory when they are exploded for a very long time under the polluted air circumstance.

Therefore, a heretofore unaddressed need exists in the art to address the aforementioned deficiencies and inadequacies.

SUMMARY OF THE DISCLOSURE

These objects, and others which will become apparent from the following disclosure, are achieved by the present disclosure which comprises in one aspect an UV/LED radiation-curable composition for forming a nail gel polish. The composition includes a photoinitiator and polyurethane acrylate oligomer, an alcohol soluble thermoplastic resin, and an acrylate monomer. The advantage of this disclosure is to remove the nail gel by alcohol-based solution, especially by a medical ethanol alcohol which is normally used for disinfection.

In one aspect of the disclosure, the UV/LED radian-curable nail gel polish composition comprises an alcohol soluble thermoplastic resin made from chemical structure $C_{13}H_{14}ClN_3S$ (labeled as "E").

In some embodiments, the UV/LED radiation curable nail gel polish compositions comprise 5-30% alcohol soluble thermoplastic resins made from chemical structure $C_{13}H_{14}ClN_3S$ (labeled as "E") that can improve a lot on alcohol removing ability.

In another aspect of the disclosure, the oligomer used are aliphatic urethane based on polyester polyol and/or polyether polyol.

In this UV/LED radiation curable nail gel polish, the composition may include ingredients such as polymers, oligomers, monomers and thixotropic additives, dispersants, defoamers, wetting additives, colorants and/or fillers, micas, glitters, etc.

In another aspect of the disclosure, the use of UV/LED radiation-curable nail gel polish could be whether a three-step gels which contain base coat, mid-layer coat and top coat, a two-step gels which contain base coat and top coat no matter which coat contains the colorant, or an one-step gel which contains only one coat is utilized. The polymerized nail gel coat with the composition of this disclosure could be easily removed by medical alcohol.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

FIG. 2 shows a flow chart of manufacturing method of the nail gel polish.

DETAILED DESCRIPTION

Figure 1:
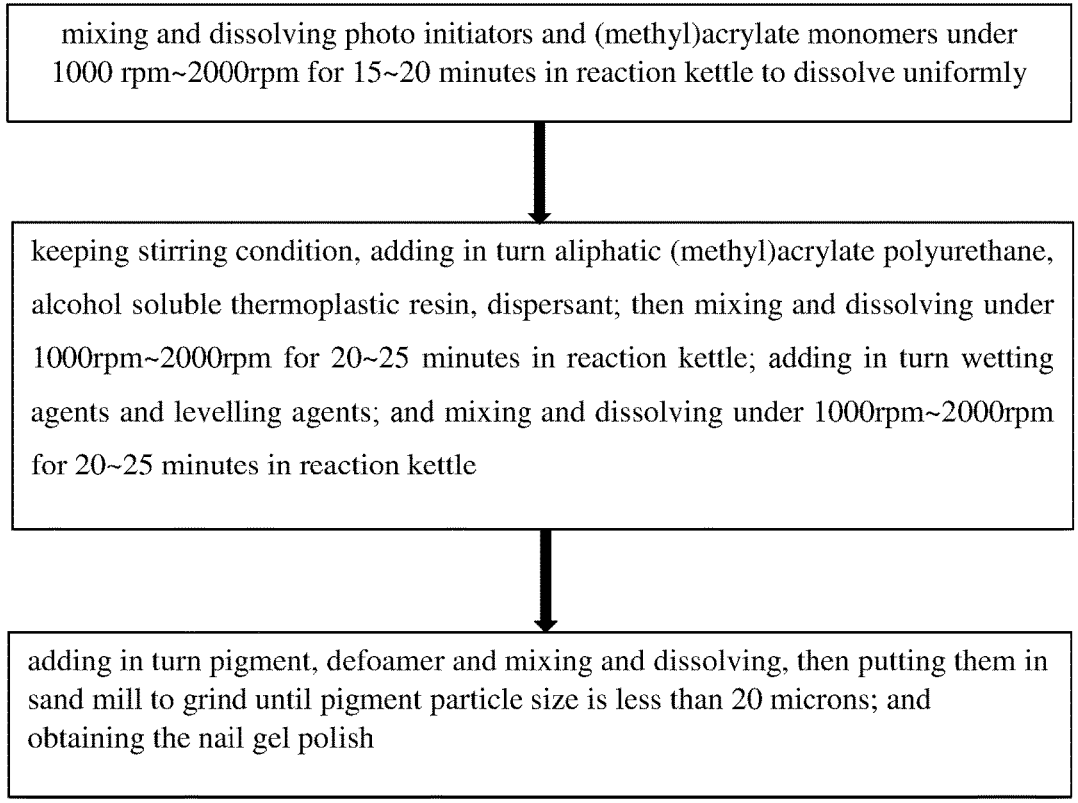
FIG. 1 shows a flow chart of preparation of a UV/LED radiation-curable nail gel polish.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It is appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It is understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It is understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It is understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It are also appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It is further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It is understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It is further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

Embodiments of the invention are illustrated in detail hereinafter with reference to accompanying drawings. It should be understood that specific embodiments described herein are merely intended to explain the invention, but not intended to limit the invention.

The use of ethanol alcohol and sometime isopropyl alcohol for disinfect purpose has been known by the general public. The medical alcohol is manufactured from plant resources and controlled by Food and Drug Administration (FDA) to protect the safety for general public. It is easy to get from local pharmacy shops of the communities, as the chemical, medical alcohol is well known as a sanitary product in house holding and antiseptic use.

This disclosure discloses a method from the composition to use the medical alcohol to remove the polymerized nail gel polish.

According to the disclosure, the nail gel polish which can be removed by medical alcohol can be successfully prepared.

The compound of this gel polish product, on one aspect, includes urethane oligomer prepared by reaction a polyol with a (methyl)acrylate monomer and one or more co-reactants selected from the group consisting of an organic diisocyanate, and a polyacid. In some embodiments, the (methyl)acrylate monomer has one polyol unit and the (methyl)acrylate oligomer has multiple polyol units.

In addition to above-described (metyl)acrylate based photo polymerized monomers, oligomers contain at least one or two unsaturated double bond. These monomers and oligomers are available from Eternal Materials Co., Ltd., RAHN AG, SARTOMER CHINA, Cytec Industries Inc., Dymax Company, etc.

The compound contains at least one special thermoplastic polymer. The polymer resin contains the molecular structure $C_{13}H_{14}ClN_3S$ (labeled as "E") is:

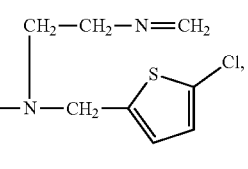

which is also known as:

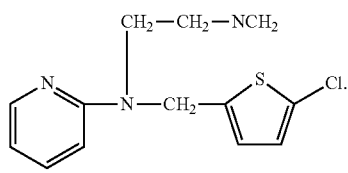

This molecular structure is easily soluble in ethanol because it contains a pyridyl group and chlorine to increase the polarity of the molecule, and the experiments prove that it is easily soluble in ethanol.

Increasing the degree of removal of the nail gel in the alcohol is the objective of the process of the product design. When we reviewed and tested the alcohol-soluble thermoplastic resins that are generally available in the market, we found out that the alcohol-soluble thermoplastic resins that are generally available in the market cannot meet the design objective. In order to improve the alcohol-soluble thermoplastic resin in the UV system, after many attempts, the present disclosure designs and finds out that the molecule E

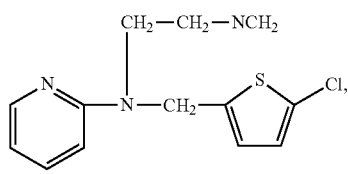

which is also

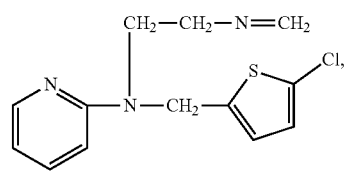 [SMILES: C=NCCN(Cc1ccc(Cl)s1)c1ccccn1]

which improves alcohol removal performance. After repeated tests, the present disclosure selects the molecular structure to specifically modify the thermoplastic resin for preparing an alcohol-soluble thermoplastic resin containing this molecular structure. The molecule E was commercialized only with the nail gel and was not for sale individually and separately.

The special nail gel polish contains a photo initiators at least one of these photo initiators which are 2-Hydroxy-2-methylpropiophenone, 1-hydroxy-cyclohexylphenyl-ketone, 4, 6-trimethylbenzoyldiphenyl-phosphine oxide or bis (2,6-difluoro-3-(1-hydropyrrol-1-yl)phenyl) titanocene, and mixtures thereof.

The special nail gel polish contains thickening agents, and has at least one of these thickening agents including fumed silica, bentonite, modified castor oil or polyamide wax.

The special nail gel polish contains levelling agents, and at least one of these levelling agents is polyether modified silicone fluid levelling or polysiloxane-polyether copolymer.

The special nail gel polish contains defoamers, and at least one of these defoamers is polysiloxane emulsion, polymer-type without organic silicon or organic modified polysiloxane.

The special nail gel polish contains wetting agents, and at least one of these wetting agents is polyether silicone or containing pigment affinity group copolymers.

The special nail gel polish contains dispersant, and includes at least one of pigment affinity group copolymers.

The pigment which can be incorporated into the concentrate includes carbon black, D&C Black No. 2, D&C Black No. 3, FD&C Blue No. 1, D&C Blue No. 4, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4., D&C Red No. 6, D&C Red No. 7, D&C Red No. 17, D&C Red No. 21, D&C Red No. 22, D&C Red No. 27, D&C Red No. 28, D&C Red No. 30. D&C Red No. 31, D&C Red No. 33,D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, titanium dioxide as well as others listed on the FDA color additives website, and Annex IV of Regulation(EC) No 1223/2009 of the European Parliament and of the Council of 30 November 2009 on cosmetic products, Coloring Agents Permitted in Cosmetics.

There are many possible embodiments of the special nail gel polish. In some embodiments, the special nail gel polish is comprised of 10-50% by weight aliphatic (methyl)acrylate polyurethane, 5-30% by weight alcohol soluble thermoplastic resin, 15-30% by weight (methyl)acrylate monomer, 1~10% by weight photo initiator, 1-5% by weight pigment, 0.1-2% dispersant, 1-5% by weight thickening agent, 0.1-1% levelling agent, 0.1-0.5% by weight defoamer agent, and 0.1-0.3% by weight wetting agent.

EXAMPLES

Example 1

Preparation of Molecular E

The synthesis routine of the molecule E is depicted as below. The two commercial available compounds A (2-aminopyridine, $C_5H_6N_2$, from Sigma-Aldrich, catalog number is A77989, and CAS Number: 504-29-0) reacted with B (2-chloro-5-(chloromethyl)thiophene, $C_5H_4Cl_2S$, from Sigma-Aldrich, catalog number is 241822, and CAS Number: 23784-96-5) to form C (n-[(5-chlorothiophen-2-yl)methyl]pyridin-2-amine, $C_{10}H_9ClN_2S$) in DMF/Et$_3$N at room temperature (RT), followed by a nucleophilic substituent reaction with ClCH$_2$CH$_2$NH$_2$ forming compound D ($C_{12}H_{14}ClN_3S$) in CH$_2$Cl$_2$. Mannish reaction between the compound D and formaldehyde (HCHO) led to the compound E ($C_{13}H_{14}ClN_3S$) in dioxane at room temperature (RT).

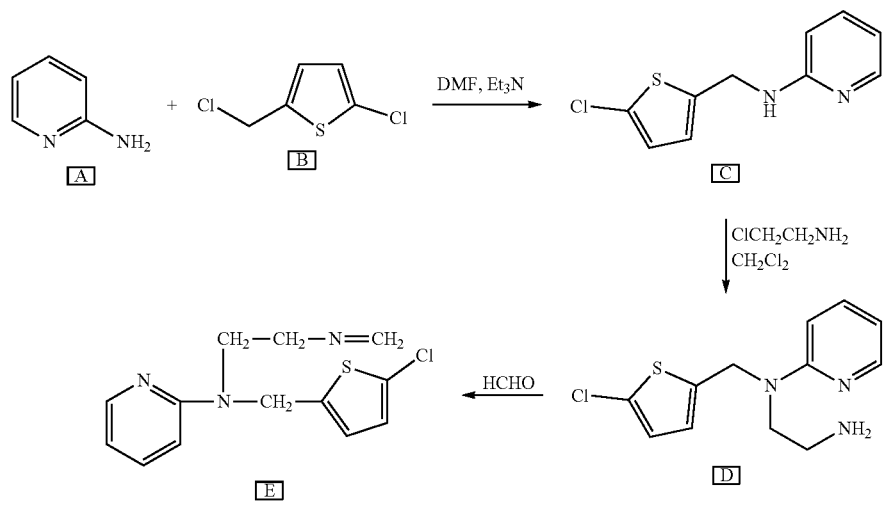
Example 2
Preparation of Alcohol Soluble Thermoplastic Resin 1, Namely $C_{60}H_{78}Cl_2N_6O_8S_2$
Compound E is a Schiff base, which is a very active electrophile and easily reacted with the compound F (Triethylene glycol bis (3-tert-butyl-4-hydroxy-5-methylphenyl) propionate, $C_{34}H_{50}O_8$, CAS #36443-68-2) to form the resin 1 ($C_{60}H_{78}Cl_2N_6O_8S2$) in dioxane at room temperature (RT).
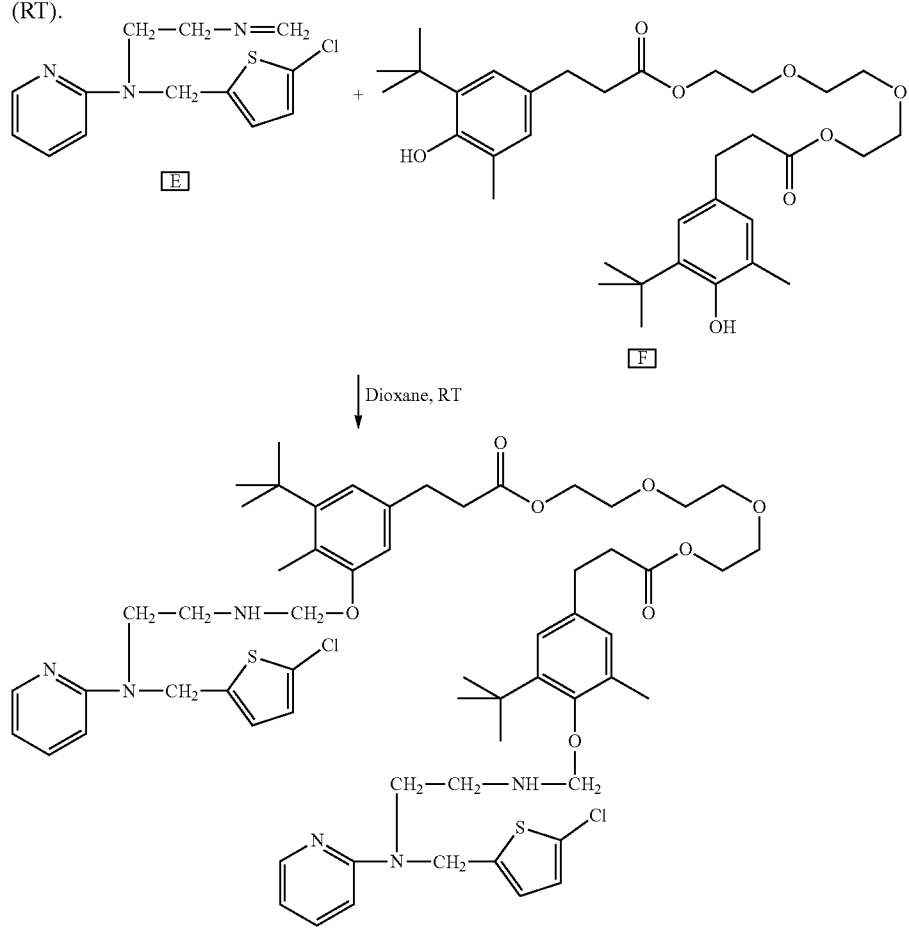

Example 3

Preparation of Alcohol Soluble Thermoplastic Resin 2, Namely (C23H26ClN3O4S2).

Similarly, the compound E reacted with the compound G (ethyl vanillate, $C_{10}H_{12}O_4$, CAS #617-05-0) to form the resin 2 C23H26ClN3O4S.

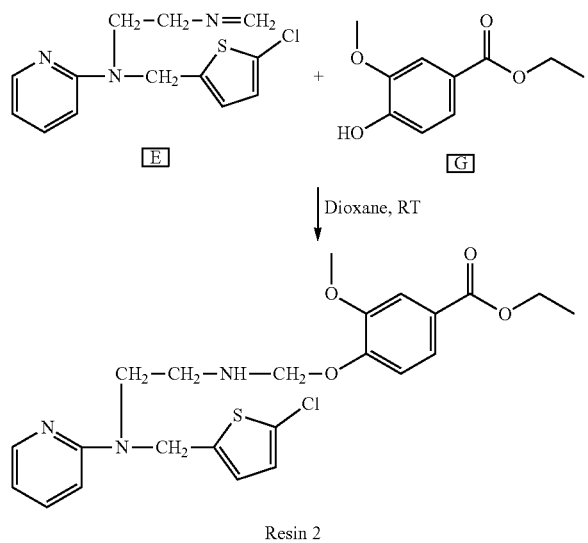

Resin 2

Example 4

Preparation of the UV/LED Radiation-Curable Nail Gel Polish, as shown in FIG. 1

(1) mixing and dissolving photo initiators and (methyl) acrylate monomers under 1000 rpm~2000 rpm for 15~20 minutes in reaction kettle to dissolve uniformly.

(2) keeping stirring condition, adding in turn aliphatic (methyl)acrylate polyurethane, alcohol soluble thermoplastic resin, dispersant, and then mixing and dissolving under 1000 rpm~2000 rpm for 20~25 minutes in reaction kettle; adding in turn wetting agents and levelling agents; and mixing and dissolving under 1000 rpm~2000 rpm for 20~25 minutes in reaction kettle.

(3) adding in turn pigment, defoamer and mixing and dissolving, and then putting them in sand mill to grind until pigment particle size is less than 20 microns. The nail gel polish is obtained.

The following non-limiting examples including all parts are listed by weight unless otherwise indicated and are presented to illustrate certain embodiments of the disclosure.

Example 4.1

| | |
|---|---|
| Aliphatic (methyl)acrylate polyurethane | 28; |
| Alcohol soluble thermoplastic resin 1 | 17; |
| Mono-functional (methyl)acrylate monomer | 15; |
| Bi-functional (methyl)acrylate monomer | 8; |
| 2,4,6-trimethylbenzoyldiphenyl-phosphine oxide | 4.6; |
| 1-hydroxy-cyclohexylphenyl-ketone | 2; |
| Bentonite | 5; |
| Polymer-type defoamer without organic silicon | 0.3; |
| Polyether modified silicone fluid levelling agent | 0.2; |
| Polyether silicone wetting agent | 0.3; |
| Red pigment | 3; and |
| Containing pigment affinity group copolymers | 0.6 |

Example 4.2

| | |
|---|---|
| Aliphatic (methyl)acrylate polyurethane | 20; |
| Alcohol soluble thermoplastic resin 1 | 20; |
| Mono-functional (methyl)acrylate monomer | 15; |
| 2,4,6-trimethylbenzoyldiphenyl-phosphine oxide | 10; |
| Bentonite | 5; |
| Polymer-type defoamer without organic silicon | 0.1; |
| Polyether modified silicone fluid levelling agent | 0.1; |
| Polyether silicone wetting agent | 0.3; |
| Red pigment | 5; and |
| Containing pigment affinity group copolymers | 0.1 |

Example 4.3

| | |
|---|---|
| Aliphatic (methyl)acrylate polyurethane | 50; |
| Alcohol soluble thermoplastic resin 1 | 10; |
| Mono-functional (methyl)acrylate monomer | 10; |
| Bi-functional (methyl)acrylate monomer | 30; |
| 2,4,6-trimethylbenzoyldiphenyl-phosphine oxide | 4; |
| 1-hydroxy-cyclohexylphenyl-ketone | 1; |
| Bentonite | 1; |
| Polymer-type defoamer without organic silicon | 0.5; |
| Polyether modified silicone fluid levelling agent | 0.1; |
| Polyether silicone wetting agent | 0.3; |
| Red pigment | 1; and |
| Containing pigment affinity group copolymers | 0.5 |

The manufacturing method of the disclosure is disclosed as following, as shown in FIG. 2:

(1) mixing and dissolving 2,4,6-trimethylbenzoyldiphenyl-phosphine oxide and 1-hydroxy-cyclohexylphenyl-ketone (photo-initiator), mono-functional (methyl)acrylate monomer and bis-functional (methyl)acrylate monomer under 1000-2000 rpm for 20 minutes in the reaction kettle until it forms uniform viscous liquid.

(2) keeping stirring condition, adding in turn aliphatic (methyl)acrylate polyurethane, alcohol soluble thermoplastic resin 1 or resin 2 or resin 3, copolymers containing pigment affinity group; then mixing and dissolving under 1000 rpm~2000 rpm for 20~25 minutes in reaction kettle; adding in turn polyether silicone wetting agent and polyether modified silicone fluid levelling agent; and mixing and dissolving under 1000 rpm~2000 rpm for 20~25 minutes in reaction kettle.

(3) adding in turn red pigment, polymer-type defoamer without organic Silicon; mixing and dissolving; and then putting them in sand mill to grind for 30 minutes until pigment particle size is less than 20 microns. The nail gel polish is obtained.

Compare the Result

To evaluate the removing the polymerized nail gel polish on human natural nails, we have bought one bottle of medical ethanol from the nearest pharmacy shop. The medical ethanol alcohol was produced by Shanghai Chenglin Chemical Co., Ltd. under the license No. (2015)-0005. The concentration of the ethanol is 75+/−5%.

Comparing Example 4.1: nail gel polish and commercial-sold nail gel polish, wherein both gel polishes are applied to the nail, after they are cured by UV light, the medical alcohol is utilized to remove. The observation is shown in Table 1.

TABLE 1

| COMPARISON | |
|---|---|
| Example 4.1 nail gel polish | Nail gel polish in bought from the market |
| After 10 min, nail gel polish is crack and can be easily removed, little hurt on finger nail. | After 10 min, nail gel is hard to remove, only with professional tool to push that nail gel can be removed. Finger nail is terribly damaged. |

Example 4.2 and 4.3 provide similar results in removing the nail gel by the medical alcohol.

The present disclosure, therefore, is well adapted to carry out the objects and attain the ends and advantages mentioned, as well as others inherent therein. While the disclosure has been depicted and described and is defined by reference to particular preferred embodiments of the disclosure, such references do not imply a limitation on the disclosure, and no such limitation is to be inferred. The disclosure is capable of considerable modification, alteration and equivalents in form and function, as will occur to those ordinarily skilled in the pertinent arts. The depicted and described preferred embodiments of the disclosure are exemplary only and are not exhaustive of the scope of the disclosure. Consequently, the disclosure is intended to be limited only by the spirit and scope of the appended claims, giving full cognizance to equivalents in all respects.

As to existing technologies the disclosure has advantages as follow: the nail gel polish refers to the disclosure abandons traditional nail polish removing methods, and adopt removing method by medical alcohol. The medical alcohol, mainly use as sanitizer, is manufactured from plant material without methanol and formaldehyde. The medical alcohol is much safer and reduces hurt on nails and skin around nails of customers and nail technicians while removing nail polish.

What is claimed is:

1. A nail gel polish, comprising the following components:
    aliphatic urethane (methyl)acrylate oligomer 15%-50% by weight;
    alcohol soluble thermoplastic resin 10%-20% by weight, wherein the alcohol soluble thermoplastic resin comprises the molecular structure as follow:

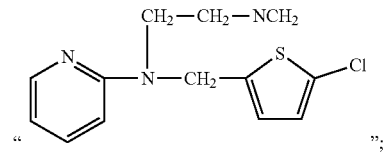

"  ";

(methyl)acrylate monomer 15%-30% by weight;
   photoinitiator 1%-10% by weight;
   pigment 1%-5% by weight
   dispersant 0.1%-2% by weight;
   thickening agent 1%-5% by weight;
   levelling agent 0.1%-4% by weight; and
   defoamer 0.1%-0.5% by weight.

2. The nail gel polish according to claim 1, wherein the (methyl)acrylate monomer is one of the monomers selected from the group consisting of mono-functional (methyl)acrylate monomer or bi-functional (methyl)acrylate monomer or the mixtures thereof.

3. The nail gel polish according to claim 1, wherein the photoinitiator is selected from the group consisting of 2-Hydroxy-2-methylpropiophenone, 1-hydroxy-cyclohexylpheyl-ketone, 2, 4, 6-trimethylbenzoyldiphenyl-phosphine oxide or bis(2,6 difluoro-3-(1-hydropyrrol-1yl)phenyl)titanocene, or mixtures thereof.

4. The nail gel polish according to claim 1, wherein the thickening agent is selected from the group consisting of fumed silica, bentonite, modified castor oil, polyamide wax, or mixtures thereof.

5. The nail gel polish according to claim 1, wherein the levelling agent is selected from the group consisting of polyether modified silicone, polysiloxane-polyether copolymer, or mixtures thereof.

6. The nail gel polish according to claim 1, wherein the defoamer is selected from the group consisting of polysiloxane emulsion, organic modified polysiloxane, or mixtures thereof.

7. The nail gel polish according to claim 1, further comprising a wetting agent, wherein the wetting agent is a polyether silicone.

8. The nail gel polish according to claim 1, wherein the aliphatic urethane (methyl)acrylate monomer is a polyfunctional polyurethane (methyl)acrylate.

* * * * *